United States Patent [19]

Kajikuri et al.

[11] Patent Number: 5,304,643

[45] Date of Patent: Apr. 19, 1994

[54] PROCESS FOR PRODUCING EPSILON-CAPROLACTAM

[75] Inventors: Hiroshi Kajikuri; Masaru Kitamura; Yasuhiko Higashio, all of Osaka, Japan

[73] Assignee: Sumitomo Chemical Company, Limited, Osaka, Japan

[21] Appl. No.: 981,474

[22] Filed: Nov. 25, 1992

[30] Foreign Application Priority Data

Nov. 27, 1991 [JP] Japan ................................ 3-312491

[51] Int. Cl.$^5$ .......................................... C07D 201/04
[52] U.S. Cl. ...................................... 540/336; 540/535
[58] Field of Search ................................ 540/535, 536

[56] References Cited

U.S. PATENT DOCUMENTS

| 3,505,958 | 3/1970 | Landis | 340/535 |
|---|---|---|---|
| 3,527,568 | 9/1970 | Immel et al. | 540/536 |
| 3,547,193 | 4/1971 | Immel et al. | 540/536 |
| 3,843,630 | 10/1974 | Fujita et al. | 540/536 |
| 4,137,264 | 1/1979 | Immel et al. | 540/536 |
| 4,248,782 | 3/1981 | Fuchs et al. | 540/536 |
| 4,267,105 | 5/1981 | Brand et al. | 540/536 |
| 4,268,440 | 5/1981 | Werther et al. | 540/536 |
| 4,968,793 | 11/1990 | Kitamura et al. | 540/536 |

FOREIGN PATENT DOCUMENTS

| 8716 | 3/1982 | European Pat. Off. | 540/536 |
|---|---|---|---|
| 234088 | 9/1987 | European Pat. Off. | 540/536 |
| 236092 | 9/1987 | European Pat. Off. | 540/536 |
| 242960 | 10/1987 | European Pat. Off. | 540/536 |
| 369364 | 5/1990 | European Pat. Off. | 540/536 |
| 380364 | 8/1990 | European Pat. Off. | 540/536 |
| 388070 | 9/1990 | European Pat. Off. | 540/536 |
| 494535 | 7/1992 | European Pat. Off. | 540/536 |
| 545789 | 10/1969 | Fed. Rep. of Germany | 540/536 |
| 1545789 | 10/1969 | Fed. Rep. of Germany | 540/535 |
| 1530845 | 11/1978 | United Kingdom | 540/536 |

Primary Examiner—Robert T. Bond
Attorney, Agent, or Firm—Cushman, Darby & Cushman

[57] ABSTRACT $\epsilon$-Caprolactam is prepared by subjecting cyclohexanone oxime in a gas phase to a catalytic reaction using zeolite catalysts in the presence of water and at least one compound selected from alcohols and ether compounds.

17 Claims, No Drawings

PROCESS FOR PRODUCING EPSILON-CAPROLACTAM

The present invention relates to a process for producing ε-caprolactam from cyclohexanone oxime using solid catalysts under gas phase reaction conditions.

ε-Caprolactam is an important raw material for nylon and the like.

The inventors have proposed processes for producing ε-caprolactam by rearrangement of cyclohexanone oxime (Beckmann rearrangement) using solid catalysts under gas phase reaction conditions (Japanese Patent Kokai Nos. Hei 2-275850 and 2-250866).

The inventors have further conducted intensive research on a rearrangement reaction of cyclohexanone oxime and have found that, when the rearrangement reaction is carried out in the presence of alcohols and/or ether compounds using zeolite catalysts and additionally in the presence of water in the reaction system, life of the catalysts is prolonged and yield of ε-caprolactam is also improved. As a result, the present invention has been accomplished.

That is, the present invention provides an industrially superior process for producing ε-caprolactam which comprises subjecting cyclohexanone oxime in a gas phase to a catalytic reaction using zeolite catalysts in the presence of water and at least one compound selected from alcohols and ether compounds.

The present invention will be explained in detail below.

The zeolite catalysts used in the present invention include, for example, crystalline silica and crystalline metallosilicate. The crystalline silica comprises substantially silicon and oxygen. The crystalline metallosilicate contains a metal in addition to silicon and oxygen, such as those which have a ratio of the number of silicon atom to that of a metal atom (Si/metal atomic ratio) of 5 or higher, preferably at least 500. As examples of the metal, mention may be made of at least one metal selected from Al, Ga, Fe, B, Zn, Cr, Be, Co, La, Ge, Ti, Zr, Hf, V, Ni, Sb, Bi, Cu and Nb. The Si/metal atomic ratio is obtained by usual analytical methods such as atomic absorption spectrometry and X-ray fluorescence analysis. These catalysts are prepared by known processes. The crystalline silica and crystalline metallosilicate have various crystalline forms and those which belong to a pentasil type structure are preferred.

The process of the present invention is characterized in that water is allowed to exist in the reaction system.

Amount of water is usually 0.06–2.5 moles, preferably 0.18–1.9 mole, more preferably 0.18–0.65 mole per mole of cyclohexanone oxime used. When amount of water is less than 0.06 mole or more than 2.5 moles per mole of cyclohexanone oxime, activity of the catalysts greatly reduces.

In the present invention, alcohols or ether compounds are allowed to exist together with water in the reaction system. The alcohols and ether compounds include those which are represented by the following formula (1):

$$R_1-O-R_2 \quad (1)$$

(wherein $R_1$ represents a lower alkyl group which may be substituted with at least one fluorine atom and $R_2$ represents a hydrogen atom or a lower alkyl or phenyl group which may be substituted with at least one fluorine atom).

Examples of the alcohols are lower alcohols of 6 or less carbon atoms such as methanol, ethanol, n-propanol, isopropanol, n-butanol, sec-butanol, isobutanol, n-amyl alcohol, n-hexanol and 2,2,2-trifluoroethanol. Methanol and ethanol are preferred. The ether compounds are preferably those which have a methyl group or an ethyl group as $R_1$ in the formula (1). Examples are ether compounds of 8 or less carbon atoms such as dimethyl ether, methylethyl ether, diethyl ether, methyl-n-propyl ether, methylisopropyl ether, methyl-tert-butyl ether and anisole. Two or more alcohols may be used. So are the ether compounds. Alcohols and ether compounds may be mixed.

In the reaction system, vapors of compounds inert to the reaction, such as benzene, cyclohexane and toluene or inert gases such as nitrogen and carbon dioxide may also be allowed to coexist as a diluent gas.

The reaction in carrying out the present invention will be explained.

The starting material cyclohexanone oxime is subjected to a catalytic reaction in the gas form. The reaction is carried out in either a fixed-bed or fluidized bed. Cyclohexanone oxime may be fed to a reactor after it is mixed with water and alcohols and/or ether compounds. Alternatively, these reactants may be fed separately. In the alternative case, water and alcohols and/or ether compounds may be fed in two or more portions. In the case of the fixed-bed reaction, it is preferred to pass a thorough mixture of these reactants through the catalyst bed.

Space velocity of the starting material cyclohexanone oxime is usually $WHSV = 0.1-40 \text{ hr}^{-1}$ (namely, feeding rate of cyclohexanone oxime per kg of the catalyst is 0.1–40 kg/hr), preferably 0.2–20 $hr^{-1}$, more preferably 0.5–10 $hr^{-1}$.

Reaction temperature is usually 250°–500° C., preferably 300°–450° C., more preferably 300°–400° C. When the temperature is lower than 250° C., reaction rate is not sufficient and selectivity of ε-caprolactam tends to decrease and when it is higher than 500° C., selectivity of ε-caprolactam tends to decrease.

The present process is carried out under pressure, atmospheric pressure or reduced pressure and is usually carried out under pressure of 0.05–10 $kg/cm^2$.

Isolation of ε-caprolactam from the reaction mixture and purification thereof are carried out, for example, by cooling and condensing the reaction product gas, followed by extraction, distillation or crystallization.

The catalyst having small activity which is caused by use for long time is easily reactivated to the initial activity by being calcined in a molecular oxygen-containing gas, for example, air stream or a molecular oxygen-containing gas to which alcohols such as methanol are added. The reactivated catalyst is repeatedly used.

According to the present invention, life of the catalysts is greatly prolonged and yield of ε-caprolactam increases.

The following nonlimiting examples explain the present invention.

REFERENCE EXAMPLE 1

Preparation of Catalyst

In a stainless steel autoclave (1.5 l) were charged tetraethylorthosilicate (Si(OC$_2$H$_5$)$_4$, 100 g, Al content: less than 10 ppm), 10% aqueous tetra-n-propylammonium hydroxide solution (224.0 g) and ethanol (214 g) and were vigorously stirred for 30 minutes. The mixed solution had a pH of 13. The autoclave was sealed and then was dipped in an oil bath in order to keep the internal temperature at 105° C. Hydrothermal synthesis was effected for 120 hours under stirring at a revolution rate of at least 400 rpm. Pressure in the autoclave reached 2-3 kg/cm$^2$. pH at the completion of the hydrothermal synthesis was 11.8. A white solid product was filtered off and washed continuously with distilled water until pH of filtrate reached about 7. The white solid was dried and calcined in an air stream at 530° C. for 4 hours to obtain powdery white crystals (27 g) which were identified to be pentasil type zeolite by powder X-ray diffractometry. Al content was 3 ppm according to atomic absorption spectroscopy assay.

To the crystals (10 g) was added 5% aqueous ammonium chloride solution (100 g) to carry out an ion exchange treatment at 50°-60° C. for 1 hour. The crystals were filtered off. The ion exchange treatment was carried out four times and then the crystals were washed with distilled water until no Cl$^-$ ion was detected in filtrate. Subsequently, the crystals were dried at 120° C. for 16 hours. The resulting crystals of ammonium salt form were shaped under pressure and sifted to obtain particles of 24-48 meshes, which were calcined at 500° C. for 1 hour in a nitrogen gas stream to obtain a catalyst.

EXAMPLE 1

In a quartz glass reaction tube (1 cm inner diameter) was packed the catalyst (0.375 g, 0.6 ml) prepared in Reference Example 1 and was preheated in a nitrogen gas stream (4.2 l/hr) at 350° C. for 1 hour. Then, to the reaction tube was fed a mixed solution of cyclohexanone oxime/methanol/water (1/6.4/0.31 in molar ratio) at a rate of 8.58 g/hr to carry out a reaction. At this time, ammonia gas and nitrogen gas were fed as carrier gases at rates of 0.21 l/hr and 3.99 l/hr, respectively. The space velocity WHSV of cyclohexanone oxime was 8 hr$^{-1}$ and temperature of the catalyst bed (reaction temperature) was 380° C. The reaction product was trapped and collected under water cooling and was analyzed by gas chromatography. The results are shown in Table 1.

The space velocity WHSV of cyclohexanone oxime, the conversion of cyclohexanone oxime and the selectivity of ε-caprolactam were calculated by the following formulas.

$WHSV\ (hr^{-1}) = O/C$

Conversion of cyclohexanone oxime
$(\%) = [(X-Y)/X] \times 100$

Selectivity of ε-caprolactam $(\%) = [Z/(X-Y)] \times 100$ wherein
O = Feeding rate (kg/hr) of cyclohexanone oxime,
C = Weight of catalyst (kg),
X = Mole number of the fed cyclohexanone oxime,
Y = Mole number of unaltered cyclohexanone oxime and
Z = Mole number of ε-caprolactam in the product.

TABLE 1

| Elapsed time (hr) | Conversion (%) | Selectivity (%) |
|---|---|---|
| 1.25 | 99.9 | 95.4 |

TABLE 1-continued

| Elapsed time (hr) | Conversion (%) | Selectivity (%) |
|---|---|---|
| 45.25 | 96.7 | 95.4 |

EXAMPLE 2

Reaction was carried out under the same conditions as in Example 1 except that a mixed solution of cyclohexanone oxime/methanol/water (1/6.4/0.1 in molar ratio) was fed to the reaction tube at a rate of 8.48 g/hr (WHSV=8 hr$^{-1}$) in place of the mixed solution of cyclohexanone oxime/methanol/water (1/6.4/0.31 in molar ratio) at a rate of 8.58 g/hr. Results of the reaction are shown in Table 2.

TABLE 2

| Elapsed time (hr) | Conversion (%) | Selectivity (%) |
|---|---|---|
| 1.25 | 92.9 | 94.2 |
| 45.25 | 79.8 | 95.2 |

EXAMPLE 3

Reaction was carried out under the same conditions as in Example 1 except that a mixed solution of cyclohexanone oxime/methanol/water (1/6.4/0.63 in molar ratio) was fed to the reaction tube at a rate of 8.73 g/hr (WHSV=8 hr$^{-1}$) in place of the mixed solution of cyclohexanone oxime/methanol/water (1/6.4/0.31 in molar ratio) at a rate of 8.58 g/hr. Results of the reaction are shown in Table 3.

TABLE 3

| Elapsed time (hr) | Conversion (%) | Selectivity (%) |
|---|---|---|
| 1.25 | 99.8 | 93.3 |
| 45.25 | 95.6 | 93.9 |

EXAMPLE 4

Reaction was carried out under the same conditions as in Example 1 except that a mixed solution of cyclohexanone oxime/methanol/water (1/6.4/1.89 in molar ratio) was fed to the reaction tube at a rate of 9.33 g/hr (WHSV=8 hr$^{-1}$) in place of the mixed solution of cyclohexanone oxime/methanol/water (1/6.4/0.31 in molar ratio) at a rate of 8.58 g/hr. Results of the reaction are shown in Table 4.

TABLE 4

| Elapsed time (hr) | Conversion (%) | Selectivity (%) |
|---|---|---|
| 1.25 | 99.1 | 94.3 |
| 45.25 | 93.2 | 94.9 |

COMPARATIVE EXAMPLE 1

Reaction was carried out under the same conditions as in Example 1 except that a mixed solution of cyclohexanone oxime/methanol (1/1.8 in weight ratio) was fed to the reaction tube at a rate of 8.44 g/hr (WHSV=8 hr$^{-1}$) in place of the mixed solution of cyclohexanone oxime/methanol/water (1/6.4/0.31 in molar ratio) at a rate of 8.58 g/hr. Results of the reaction are shown in Table 5.

Water content in the starting material cyclohexanone oxime was analyzed to obtain 0.3% by weight. This corresponded to 0.019 mole per mole of the cyclohexanone oxime.

TABLE 5

| Elasped time (hr) | Conversion (%) | Selectivity (%) |
|---|---|---|
| 1.25 | 96.8 | 93.5 |
| 45.25 | 58.7 | 95.2 |

COMPARATIVE EXAMPLE 2

Application to Boric Acid Catalyst

Reaction was carried out under the same conditions as in Example 1 except that 0.375 g of boric acid was used in place of the catalyst prepared in Reference Example 1. Immediately after a reaction started, boric acid was dissolved out and substantially no reaction occurred.

What is claimed is:

1. A process for producing ε-caprolactam which comprises subjecting cyclohexanone oxime in a gas phase to catalytic reaction using zeolite catalysts in the presence of water and at least one compound selected from alcohols and ether compounds.

2. A process according to claim 1, wherein the zeolite catalyst is a crystalline silica.

3. A process according to claim 1, wherein the zeolite catalyst is a crystalline metallosilicate.

4. A process according to claim 3, wherein the crystalline metallosilicate has a Si/metal atomic ratio of 5 or more.

5. A process according to claim 4, wherein the metal is at least one element selected from Al, Ga, Fe, B, Zn, Cr, Be, Co, La, Ge, Ti, Zr, Hf, V, Ni, Sb, Bi, Cu and Nb.

6. A process according to claim 1, wherein the zeolite catalyst has a pentasil type structure.

7. A process according to claim 1, wherein amount of the water is 0.06–2.5 moles per mole of the cyclohexanone oxime.

8. A process according to claim 1, wherein the alcohols and ether compounds are those having the formula (1): $R_1-O-R_2$ (wherein $R_1$ represents a lower alkyl group which may be substituted with at least one fluorine atom and $R_2$ represents a hydrogen atom, or a lower alkyl or phenyl group which may be substituted with at least one fluorine atom).

9. A process according to claim 8, wherein the compound represented by the formula (1) is at least one compound selected from the group consisting of lower alcohols of 6 or less carbon atoms and ether compounds of 8 or less carbon atoms.

10. A process according to claim 9, wherein at least one compound selected from the group consisting of the lower alcohols of 6 or less carbon atoms and the ether compounds of 8 or less carbon atoms is at least one compound selected from the group consisting of methanol and ethanol.

11. A process according to claim 1, wherein space velocity of cyclohexanone oxime is $0.1-40\ hr^{-1}$.

12. A process according to claim 1, wherein reaction temperature is 250°–500° C.

13. A process according to claim 1, wherein reaction pressure is $0.05-10\ kg/cm^2$.

14. A process according to claim 1, wherein the zeolite catalyst having small activity which is caused by use for long time is reactivated by being calcined in a molecular oxygen-containing gas.

15. A process according to claim 14, wherein the molecular oxygen-containing gas is air.

16. A process according to claim 14, wherein the molecular oxygen-containing gas contains alcohols.

17. A process according to claim 16, wherein the alcohol is methanol.

* * * * *